(12) United States Patent
Blank

(10) Patent No.: US 6,479,076 B2
(45) Date of Patent: Nov. 12, 2002

(54) NICOTINE DELIVERY COMPOSITIONS

(76) Inventor: Izhak Blank, 4 Simtat Arnon, Kiriat Ono 55000 (IL)

( * ) Notice: Subject to any disclaimer, the term of this patent is extended or adjusted under 35 U.S.C. 154(b) by 0 days.

(21) Appl. No.: 09/760,203

(22) Filed: Jan. 12, 2001

(65) Prior Publication Data

US 2002/0131993 A1 Sep. 19, 2002

(51) Int. Cl.⁷ .......................... A61K 9/14; A61K 15/16; A61K 9/70
(52) U.S. Cl. ...................... 424/484; 424/487; 424/447; 424/448; 424/449; 424/443
(58) Field of Search .................................. 424/484, 447, 424/449, 422, 423, 424, 426, 448, 486, 443, 487

(56) References Cited

U.S. PATENT DOCUMENTS

| | | |
|---|---|---|
| 2,776,924 A | 1/1957 | Matin |
| 3,214,338 A | 10/1965 | Ehrlich |
| 3,287,222 A | 11/1966 | Larde et al. |
| 3,608,070 A | 9/1971 | Nouvel |
| 3,972,995 A | 8/1976 | Tsuk et al. |
| 4,210,633 A | 7/1980 | Takruri et al. |
| 4,908,213 A * | 3/1990 | Govil et al. ................. 424/447 |
| 5,128,138 A | 7/1992 | Blank |
| 5,232,703 A | 8/1993 | Blank |
| 6,024,976 A * | 2/2000 | Miranda et al. ............. 424/449 |
| 6,238,284 B1 * | 5/2001 | Dittgen et al. .............. 424/443 |

FOREIGN PATENT DOCUMENTS

| | | |
|---|---|---|
| DE | 1 467792 | 12/1968 |
| DE | 26 34 004 | 2/1978 |
| GB | 1380171 | 8/1975 |

* cited by examiner

*Primary Examiner*—Thurman K. Page
*Assistant Examiner*—Blessing Fubara
(74) *Attorney, Agent, or Firm*—Amster, Rothstein & Ebenstein

(57) ABSTRACT

A composition containing nicotine and an uncrosslinked, water-insoluble vinylpyrrolidone copolymer is applied on the skin of patients in the form of a gel, ointment, solution, suspension or film which slowly releases nicotine and creates levels of the drug in the blood to reduce nicotine-craving in smokers, thereby assisting in smoking-cessation programs.

21 Claims, No Drawings

NICOTINE DELIVERY COMPOSITIONS

BACKGROUND OF THE INVENTION

This invention relates to a new method for transdermal nicotine delivery which is particularly useful as a smoking-cessation aid in the treatment of addition to cigarette smoking.

Nicotine is the most widely used additive drug. Nicotine is more addictive than heroin, cocaine and alcohol. Every year, 30% of the smokers try to get rid of the habit but only about 3% succeed. In the United States alone there are 50 million smokers, each consuming an average of 10,000 cigarettes a year. This is estimated to cause 420,000 deaths due to lung and heart diseases and cancer. There are at present 1.1 billion smokers in the whole world and the World Health Organization has indicated that by the year 2020 tobacco related illness will be the cause of around 10% of all diseases affecting mankind and will be responsible for 14% of all deaths. The use of tobacco products produces a yearly loss of 200 billion dollars to the economy.

In Israel the problem is quite severe. Recent data shows that 28% of adults and 18% of youngsters (below 18 years old) are smokers. It is estimated that every year 10,000 people die due to the smoking habit and another 1,400 die due to passive smoking. Life insurance companies charge approximately double premium payments to smokers as compared to non-smokers. For a one million shekel life insurance policy ($=4 shekel) a 50 year old man will pay 6,690 shekel if he is a smoker and only 3,540 shekel if he is not.

Nicotine is by itself a moderately toxic material but in the case of cigarette smoking it is not the direct killer. The high temperature at the tip of the cigarette converts tobacco into 4,000 compounds. Of these, 400, including nicotine and carbon monoxide, are toxins, and another 40 are carcinogens (C&EN Nov. 28, 1994). Delivery of these products to the lungs is very effective since they are in the form of an extremely fine aerosol, and only 5–10 seconds after inhaling the nicotine arrives to the brain, dopamine is released and produces a quick pleasurable feeling.

Breaking the addiction to cigarette smoking can be aided by delivering the drug to the body in small controlled quantities, not through the lungs but through the skin, in the form of nicotine containing patches. Other less used presentations currently marketed deliver nicotine via mucous tissues; these are in the form of chewing gum, nicotine inhalers and nicotine nasal sprays. In all cases the use of Nicotine Replacement Treatment (NRT) is designed to satisfy the craving for the drug without generating the toxic and carcinogenic materials related to smoking.

There are many reports in the literature that these methods are helpful in considerably increasing the percentage of successful smoking cessation. However, each of the pharmacological methods available at present have certain problems:

Nicotine patch (Transdermal Nicotine System).—The most popular patches come in 3 sizes containing 7, 14 and 21 mg of nicotine. The smoker starts with the 21 mg patch for several weeks and then goes over to the 14 mg. patch for another few weeks. Weaning is completed by using the 7 mg. patch. The patches have proven to be effective and studies show that they double the odds of being abstinent at 6 and 12 months as compared to placebo patches. The main problems related to the use of patches are mild to moderate dermatological reactions in a significant proportion of patients. Patches occlude the area of the skin where they are applied. Allergenic reactions may be produced. The patches are quite expensive and this deters their use by a large part of the population.

Nicotine gum (nicotine polacrilex).—In this device the nicotine is bound to an ion-exchange resin and incorporated into a gum base. For its proper performance the gum has to be alternatively chewed and parked in the mouth until complete depletion of the nicotine. Two forms of this device are available, containing 2 or 4 mg of nicotine. A smoker will have to chew one gum approximately every two hours in order to attenuate the nicotine craving during the treatment period. The side effects may be: sore throat, sore jaw, nausea and vomiting. It is not recommended to use it with dentures, and there are indications that Mercury may be leached out from fillings.

Nicotine nasal spray.—This consists of a nicotine solution contained in a small bottle fitted for insertion into the nostril. By pressing the pump mechanism in the bottle, a fine spray of nicotine (0.5 mg) is released into the nostril. The patient squirts once in each nostril for a total of 1 mg of nicotine. Typically, a patient will use 13 to 20 doses per day. The long term effectiveness of the nasal spray has been shown in clinical tests. The most common side-effects are: nasal and sinus irritation, funny nose, watery eyes, throat irritation, sneezing and coughing. This device is expensive, and its use is very limited.

Nicotine inhaler.—This is a nicotine (10 mg) impregnated plug, that is inserted into a cigarette-like tube or mouthpiece. The patient puffs on the mouthpiece, the air becomes saturated with nicotine and is then inhaled by the user. The nicotine is absorbed mainly via the buccal mucosa. Adverse effects reported are mild mouth and throat irritation and coughing. The use of this device is not very popular.

The present invention consists of an improved transdermal nicotine delivery system which overcomes the problems related to the use of patches, gum, nasal spray and inhaler during smoking-cessation treatments, wherein topical application of the compositions on the skin will provide a slow and sustained release of nicotine so as to maintain the desired level in the blood of the patient and thus alleviate his craving for the drug. This is accomplished by the incorporation of uncrosslinked, water-insoluble N-vinylpyrrolidone copolymers in the compositions. The terms N-vinylpyrrolidone and vinylpyrrolidone are interchangable in this text.

The preferred system consists of an alcoholic gel containing nicotine and a copolymer together with excipients useful for improving the viscosity and texture of the gel and eliminating irritation. The gel is packed in an aluminum can provided with a dosifying pump which delivers an exact amount of gel every time the actuator is pressed. The gel is uniformly distributed over a small area of skin by means of a cap which is part of the package. Upon deposition on the skin as a thin layer, the gel dries quickly leaving an invisible film of polymer containing nicotine from which the drug leaches out gradually into the skin.

The patient can regulate the quantities applied according to his own needs. For instance, if every actuation of the pump delivers a quantity of gel containing 8 mg of nicotine, the user can start the treatment by applying 3 doses (24 mg) and go down gradually as he needs and less nicotine to complete the smoking-cessation treatment. This possibility of flexible dosage is very important since the nicotine-craving of the smoker varies according to his own individual physical and psychological status at different times.

The use of transdermal nicotine in this form may also be useful, as a dopamine release agent, in the treatment of other conditions such as attention deficit hyperactive disorder (ADHD), attention deficit disorder (ADD), Tourette's syndrome, schizophrenia, Parkinson's disease, anxiety and depression.

The use of water-soluble polyvinylpyrrolidone in conjunction with other medicaments has been disclosed in a number of patents. Thus, U.S. Pat. No. 3,972,995 discloses a buccal dosage form in which the water-soluble homopolymer functions as a binder in an adhesive layer. U.S. Pat. No. 3,214,338 discloses a topical ointment in which the water-soluble homopolymer is added to an emulsifiable polyvinyl acetate powder. U.S. Pat. No. 3,803,300 discloses a film-forming ointment containing water-soluble vinylpyrrolidone homopolymer or copolymers. U.S. Pat. No. 3,287,222 discloses the use of the homopolymer as a water-soluble plasticizer in an impregnating solution for a synthetic fiber medical dressing. U.S. Pat. No. 4,210,633 discloses a water-soluble medicated film containing the water-soluble homopolymer. U.S. Pat. No. 3,608,070 discloses a surgical dressing which is an ointment containing a vinylpyrrolidone copolymer, a thixotropic agent, a water-soluble plasticizer and a solvent such as aqueous ethanol. The film formed on drying the ointment is readily soluble in water. U.S. Pat. No. 2,776,924 discloses the use of water-soluble polyvinylpyrrolidone to inhibit adverse reactions from therapeutic agents in topical applications.

In these prior art disclosures with medicaments N-vinylpyrrolidone polymers are used because of their film-forming ability and/or water solubility. The rapid solubilization of the polymer results in rapid release of the medicament.

The prior art discloses that the use of water-insoluble, crosslinked polyvinylpyrrolidone also promotes the rapid release of medicament. Thus, British Patent No. 1,3S0,171 discloses the use of crosslinked, water-insoluble polyvinylpyrrolidone in medicinal tablets containing a drug, to promote rapid disintegration of the tablet in aqueous fluids and increase the availability of the drug. Examples are provided which illustrate that the presence of water-insoluble polyvinylpyrrolidone results in more rapid disintegration and release of the drug as compared with the water-soluble polymer. German Patent Application 2,634,004 discloses the use of cross-linked, insoluble polyvinylpyrrolidone as a carrier material for poorly soluble medicaments in order to accelerate the release thereof when administered orally. German Patent Application 1,467,792 discloses the use of crosslinked polyvinylpyrrolidone as a disintegration agent to increase the rate of disintegration of a tablet to promote the extremely rapid release of the drug therein in the digestive tract.

Insolubilization of a polymer by crosslinking reduces its capacity for drug solvation. In our case we obtain water-insoluble copolymers by copolimerizing vinylpyrrolidone with a suitable proportion of an hydrophobic comonomer which also allows a better retention of the drug in the copolymer film deposited on the skin.

SUMMARY OF THE INVENTION

The prior art teaches that water-soluble polyvinylpyrrolidone in the solid state acts as a solubilizer and may quicken the availability of a drug. In some instances, the use of crosslinked water-insoluble polymers has been described as useful for the same purpose. It is known that crosslinked polymers or copolymers are poor solvents. In fact, crosslinking is used to increase stability of polymers against solvents and other chemicals, and therefore drugs are less soluble in crosslinked polymers than in linear ones.

In the present invention we use copolymers which are water-insoluble due to their particular composition and are not crosslinked. They are therefore good solvents for drugs.

Surprisingly, it has now been discovered that the incorporation of an uncrosslinked, water-insoluble vinylpyrrolidone copolymer in an ointment, gel or film containing nicotine permits a slow release of the drug when applied topically to the skin.

It has further been discovered that the delivery of nicotine from a composition which contains a water-insoluble linear polyvinylpyrrolidone copolymer maintains blood levels of the drug at the concentrations required for clinical efficacy.

It has further been discovered that gels, ointments and films with sustained release characteristics can be prepared by the admixture of a dispersion or solution of a water-insoluble vinylpyrrolidone copolymer with nicotine and a conventional vehicle such as ethanol, isopropanol, petrolatum, lanolin and other such vehicles and excipients used in pharmaceutical and cosmetic compositions.

It has further been discovered that films with sustained release characteristics can be prepared from a solution in ethanol containing a water-insoluble vinylpyrrolidone copolymer and nicotine, wherein the solution is applied to the skin per se or after thickening with suitable excipients.

DETAILED DESCRIPTION OF THE INVENTION

According to the present invention, it has now been found that important advantages and improvements over prior art compositions and pharmaceutical presentation forms containing nicotine and methods of topical application thereof can be obtained by admixture with an uncrosslinked, water-insoluble vinylpyrrolidone copolymer.

Water-insoluble copolymers of vinylpyrrolidone, which can be used in the practice of this invention, may be prepared by the copolymerization of vinylpyrrolidone with one or more appropriate comonomers in the proportions which yield water-insoluble, uncrosslinked copolymers. Suitable comonomers include acrylic esters, methacrylic esters, vinyl esters, crotonic esters, vinyl ethers, maleic half esters and diesters, vinylene carbonate, styrene, allyl esters, allyl ethers, etc. Other comonomers which are capable of copolymerizing with vinylpyrrolidone and are well known to those skilled in the art may also be used. Toxicological considerations restrict the choice of monomers to those which yield copolymers having a demonstrated lack of toxicological side-effects on topical application to the skin, good drug compatibility, good adhesion to the skin and film-forming properties.

The acrylic, methacrylic, crotonic and maleic esters which may be used in the preparation of the water-insoluble vinylpyrrolidone copolymers which are effective in the practice of the present invention, include the esters of $C_1$–$C_{40}$ linear, branched or cyclic alkanols, aralkanols, phenols and substituted phenols. The co-polymers of vinylpyrrolidone and the acrylic, methacrylic, crotonic and maleic esters may be made by copolymerization of vinylpyrrolidone with the appropriate ester or by esterification of copolymers of vinyl~ pyrrolidone and acrylic, methacrylic, crotonic and maleic acid or anhydrides, with the appropriate hydroxylcontaining compound~ Unesterified carboxylic acid functionality may be retained in the copolymer.

The vinyl esters and allyl esters which may be used in the preparation of the water-insoluble vinylpyrrolidone copolymers which are useful in the practice of this invention, include the esters of $C_1$–$C_{40}$ linear, branched or cyclic aliphatic, araliphatic or aromatic carboxylic acids. The copolymers of vinylpyrrolidone and the vinyl esters may be prepared by copolymerization of vinylpyrrolidone with the appropriate vinyl ester or by transesterification of copolymers of vinylpyrrolidone and vinyl acetate or other vinyl esters or by esterification of hydrolyzed copolymers of vinylpyrrolidone and vinyl acetate or other vinyl esters. The copolymers of vinylpyrrolidone and allyl esters may also be prepared either by direct copolymerization or by transesterification or esterification, analogous to the preparation of vinyl ester copolymers with vinylpyrrolidone.

Graft copolymers made by grafting vinyl monomers onto polyvinylpyrrolidone may also be used, e.g. graft copolymers of polyvinylpyrrolidone with acrylic esters, methacrylic esters, styrene, vinyl acetate and the like.

The water-insoluble copolymers of vinylpyrrolidone which be used in the practice of the present invention, may be prepared by any of the conventional methods known in the art, including bulk, solution, emulsion, suspension or dispersion polymerization, with appropriate free radical catalysts such as peroxygen compounds, azo compounds, redox systems, radiation and other catalytic techniques for initiating free radical polymerization. Since the method of polymerization is not an integral part of the practice of the present invention, any suitable method known to those skilled in the art may be used.

The amount of one or more comonomers in the water-insoluble vinylpyrrolidone copolymers which are useful in the practice of the present invention may be varied from 20% to 80% by weight. The actual amount is determined by the nature of the comonomer and the concentration necessary to produce a water-insoluble copolymer.

The drug used in the practice of the present invention may be nicotine or its salts and also cotinine. The preferred drug is nicotine.

The compositions described in this application are particularly effective as aids in smoking-cessation programs. They can also be potentially useful in the treatment of attention deficit hyperactive disorder, Tourette's syndrome, schizophrenia, anxiety and depression.

The nicotine compositions which are useful in the practice of the present invention and provide sustained release of the drug, may be prepared by dissolving or dispersing the water-insoluble vinylpyrrolidone copolymer in a solvent such as ethanol, isopropanol, vegetable oils and petrolatum and admixing the polymer solution or dispersion with nicotine.

The solution, or dispersion, of the uncrosslinked water-insoluble vinylpyrrolidone copolymer and nicotine, in the presence or absence of an excipient, may be cast on a suitable surface and the solvent evaporated under ambient pressure or in vacuo, at ambient or slightly elevated temperature. The resultant film on the substrate surface or after removal from the substrate, contains nicotine and may be cut into strips or tapes which can be affixed to the skin of a patient for sustained release of the medicament.

The solution or dispersion of uncrosslinked, water-insoluble vinylpyrrolidone copolymer and nicotine may be applied directly to the skin of the patient and permitted to evaporate to form a film thereon, containing nicotine. The latter is slowly released from the film and absorbed into the skin of the patient.

A gel or thickened solution of nicotine and water-insoluble vinylpyrrolidone copolymer may be applied with greater control to a restricted area of skin than a low viscosity solution. The solution may be thickened by the addition of a small amount of a soluble high molecular weight natural or synthetic thickener or a cellulose derivative thickener of the type well known to those skilled in the art.

High surface area inorganic materials such as finely divided fumed silica are also effective thickeners. The addition of a small amount of such a material results in a marked increase in the viscosity of the solution. The resultant gel or thickened solution is thixotropic and flows readily during application but does not run after application to the skin. The large surface area of the silica thickener increases the rate of evaporation of the solvent and contributes to rapid drying and film formation. Nicotine in the formulation is slowly released and absorbed into the skin of the patient. At the end of the treatment time, the film may be removed by washing with soap and water.

The gel or thickened solution may be applied to the skin in a pre-measured amount from a tube, a roll-on dispenser, a graduated spatula or via a dosifying pump.

The solution of nicotine and water-insoluble vinylpyrrolidone copolymer in ethanol may be pressurized in an aerosol can and nicotine may be conveniently applied to the skin using an aerosol formulation containing one or more low boiling propellants.

In order to control the amount of polymer and nicotine applied to the skin, it is advantageous to use a metering valve which delivers precise quantities of solution. When applied in this manner, the propellant and solvent quickly evaporate leaving a dry film of controlled nicotine content covering the desired area of skin.

A solution or dispersion of uncrosslinked, water-insoluble vinylpyrrolidone copolymer and nicotine, in the absence or presence of an excipient, may be applied to a porous or open-structured substrate such as gauze, bandage tissue or paper, and upon evaporation of the solvent, provides an impregnated structure containing nicotine, which is released over an extended period of time when applied topically to the skin of a patient.

The solution or dispersion of water-insoluble vinylpyrrolidone copolymer and nicotine may be mixed, with stirring, with one or more ointment bases, such as petrolatum, vasoline, lanolin, stearin, spermaceti wax or other waxy or fatty material. The ointment may be applied directly to the skin of a patient or may be coated on a carrier such as a bandage or polymeric tape for topical application to the skin of a patient. The nicotine is slowly released and absorbed into the skin of the patient over an extended period of time. Although the vinylpyrrolidone copolymer is water-insoluble, the hydrophilicity of the vinylpyrrolidone units contained therein results in moisture absorption, e.g. from perspiration on the skin of the patient, and facilitates release of the nicotine from the composition into the skin. The rate of release may be varied over a wide range and is dependent upon the percentage of vinylpyrrolidone in the copolymer and the ratio between the copolymer and nicotine.

The concentration of water-insoluble vinylpyrrolidone copolymer and nicotine in the compositions of the present invention, may be varied over a wide range, depending upon the desired release rate. The nicotine concentration may range from about 0.1% to about 10% of the total weight of the composition, while the concentration of the water-insoluble vinylpyrrolidone copolymer may range from about 3 to about 20% of the weight of the formulation.

The following examples are non-limiting illustrative embodiments of the compositions and methods of the present invention. Variations thereof will be obvious to those skilled in the art.

EXAMPLE I

The emulsion copolymerization of 66.7 parts of N-vinylpyrrolidone (VP) and 28.6 parts of lauryl methacrylate (LM) was carried out in 200 parts of water containing 5 parts of sodium stearate and 1.25 parts of 30% hydrogen peroxide as catalyst. The mixture was heated with stirring and the polymerization was carried out at 75° C. for about 10 hours. The conversion was 92%. The emulsion was spray dried at about 210° C. to yield a fine, off-white powder. The nitrogen content of the copolymer was 8.6%, indicating a VP content of 68%.

EXAMPLE II

An emulsion polymerization was carried out using the following ingredients, in parts by weight:

| | |
|---|---|
| Water | 22,100 |
| Stearic acid | 440 |
| Ammonium Hydroxide (25%) | 192 |
| Isopropanol | 112 |
| N-Vinylpyrrolidone | 8,064 |
| Lauryl methacrylate | 3,456 |
| Sodium metabisulfite (6% aq. solution | 425 |
| Hydrogen peroxide (30%) | 156 |

In this formulation ammonium stearate is the emulsifier although other emulsifiers may be used. All the ingredients, except the sodium metabisulfite solution, were charged into a stainless steel reactor equipped with heating jacket, condenser and mechanical stirrer. The bisulfite solution was added slowly over 5 hours while maintaining the temperature at 75° C. with stirring. The reaction was then continued with stirring for an additional 4 hours at 75° C. and then the emulsion was allowed to cool to room temperature. The solids content was 32.5%, representing 94% conversion. The emulsion was diluted to 20% solids and spray dried at 210° C. to yield a fine off-white powder which had a nitrogen content of 8.7%, equivalent to a VP content of 69%.

EXAMPLE III

A copolymer batch was prepared by using the following charge:
Water 80 liter
Ammonium hydroxide (28%) 0.39 liter
Ammonium salt of a sulfated ester of alkyphenoxypoly (ethyleneoxy)ethanol 1.57 Kg
N-vinylpyrrolidone 32.0 Kg
Lauryl methacrylate 13.8 Kg
Hydrogen peroxide (30%) 1.16 liter
Sodium metabisulfite 0.18 Kg. (dissolved in 2 liter water)

After completing the reaction and drying, as described in example II, the material had a nitrogen content of 8.3%, as shown by the Kjeldahl method, equivalent to a VP content of 65.8%. The completion of the reaction was checked by the free monomers content, which was: Vinyl pyrrolidone 0.22% free monomer and Lauryl methacrylate also 0.22% free monomer, both determined by gas chromatography.

EXAMPLE IV (B2878)

A gel base was prepared by vigorously mixing the following ingredients (in parts by weight):

| | |
|---|---|
| Copolymer of example III | 6.75 |
| (Propylene glycol | |
| Hydroxypropyl cellulose | |
| Isopropyl myristate | |
| Stearic acid | |
| Cetyl alcohol | |
| Fumed silica) | 12.45 |
| Ethanol | 80.80 |

The resultant gel had a viscosity of 12,000 cps and a specific gravity of 0.8.

EXAMPLE V

To 40 g of gel of example IV were added 140 mg of nicotine. Mixed thoroughly to obtain a composition containing 3.5 mg/g (2.8 mg/ml). This composition was used for pharmacokinetic trials with rats.

30 Sprague Dawley male rats weighing approximately 250 g. were used in a pharmacokinetic trial. To each animal were applied daily 0.3 ml (0.24 g) of the gel, containing 0.84 mg nicotine, on a shaved area of the back. Blood samples were taken and plasma levels of cotininine were determined. Cotinine is a stable metabolite of nicotine, easy to detect, and present at a concentration of 10 times the concentration of nicotine. It is used as a standard marker for the drug. In the case of the present test, made over a period of 96 hours, average cotinine levels in the plasma of the animals were around 200 ng/ml, equivalent to approximately 20 ng/ml of nicotine.

EXAMPLE VI

Typically concentrations of nicotine in plasma start being significant shortly after application. They achieve a maxima at around 6 hours after application and gradually decrease after 24 hours, when a new application is due. Thus in another trial made with 45 rats, similarly to the one described in example IV, but over a period of 5 days, concentrations of cotinine in the plasma on the fourth day of the trial were as shown are in the table below:

| Time after application Hours | cotinine in plasma ng/ml | nicotine equivalent ng/ml |
|---|---|---|
| 2 | 451 | 45 |
| 4 | 483 | 48 |
| 6 | 574 | 57 |
| 16 | 260 | 26 |
| 24 | 112 | 11 |

EXAMPLE VII

To 49 g. of a gel base prepared as per example IV were added 1.75 g. of nicotine to obtain a composition containing 35 mg/g (28 mg/ml) of the drug. This was used in a pilot clinical test using three healthy volunteers. One a heavy smoker, one a a light smoker and one a non-smoker. The smokers were requested to abstain from smoking for at least 4 days before the trial. On each volunteer 0.5 ml of the gel, containing 14 mg. nicotine, was applied at 8 a.m. Urine samples were taken before application and subsequently at four and 24 hours:

|  | Heavy smoker | light smoker | non smoker |
|---|---|---|---|
|  |  | Cotinine in urine, ng/ml |  |
| Before application | 441 | 69 | 9 |
| After 4 hours | 434 | 100 | 42 |
| After 24 hours | 223 | 134 | 82 |

It can be seen that the heavy smoker did not comply and had smoked during the wash off period, but the test proves that the transdermal composition has a long acting effect. The light smoker and non-smoker show moderate levels of nicotine in the urine.

What is claimed is:

1. A composition for the sustained transdermal delivery of nicotine, comprising a gel, ointment, solution, suspension or film, containing a mixture of nicotine and an uncrosslinked, water-insoluble vinypyrrolidone copolymer containing at least 20% vinylpyrrolidone and an hydrophobic comonomer which is copolymerizable therewith, wherein the nicotine concentration is within the range of 0.1 to about 10% of the total weight of the composition.

2. A composition for the sustained transdermal delivery of nicotine comprising a gel, ointment, solution, suspension or film, containing a mixture of nicotine and an uncrosslinked, water-insoluble vinypyrrolidone copolymer containing at least 20% vinypyrrolidone and an hydrophobic comonomer consisting of an ester prepared from an unstatured acid selected from the group which includes acrylic acid, methacrylic acid, crotonic acid, maleic acid, and the corresponding anhydrides wherein the nicotine concentration is within the range of 0.1 to about 10% of the total weight of the composition.

3. The composition of claim 2 for use in smoking-cessation programs.

4. The composition of claim 2 for use in the treatment of Tourette's syndrome, schizophrenia, Parkinson's disease, attention deficiency, Alzehimer disease, anxiety and depression.

5. The composition of claim 2, wherein the ester is selected from the group consisting of the acrylic and methacrylic esters of C1 to C40 linear and branched alkanols.

6. The composition of claim 2, wherein the ester is lauryl methacrylate.

7. The composition of claim 2, wherein the ester is 2-ethylhexl acrylate.

8. The composition of claim 1 wherein the ester is vinyl acetate.

9. The composition of claim 1 where the vinypyrrolidone in the copolymer is 35–75% by weight.

10. The composition of claim 1 where the nicotine is 0.2–6% by weight of the composition.

11. A composition for smoking-cessation treatment by controlled transdermal delivery of nicotine consisting of a gel containing nicotine and an uncrosslinked, water-insoluble vinypyrrolidone copolymer with an hydrophobic comonomer wherein the copolymer contains at least 60–70% by weight vinypyrrolidone, the comonomer being a methacrylic or acrylic ester.

12. A composition for the sustained transdermal delivery of nicotine, comprising a gel, ointment, solution, suspension or film, containing a mixture of nicotine and an uncrosslinked, water-insoluble vinypyrrolidone copolymer containing at least 20% vinypyrrolidone and an hydrophobic comonomer which is copolymerizable therewith, wherein the nicotine concentration is within the range of 2 to about 15% of the total weight of the composition.

13. The composition of claim 1 where the nicotine and water-insoluble vinypyrrolidone copolymer are combined with an ointment base.

14. A bandage, gauze or tape impregnated or coated with the composition of claim 2.

15. The composition of claim 1 where nicotine and water-insoluble vinypyrrolidone copolymer are combined with a solvent and a thickener to generate a gelled composition.

16. A method for providing for the sustained transdermal administration of nicotine which comprises applying to the skin of a patient a solution containing the drug and an uncrosslinked water-insoluble vinypyrrolidone copolymer which contains at least 20% by weight of vinypyrrolidone and a comonomer which is copolymerizable therewith by free radical polymerization.

17. The composition of claim 1 wherein the nicotine is in the form of a salt.

18. The composition of claim 2 wherein the nicotine is in the form of a salt.

19. The composition of claim 11 wherein the nicotine is in the form of a salt.

20. The composition of claim 12 wherein the nicotine is in the form of a salt.

21. The method of claim 16 wherein the nicotine is in the form of a salt.

* * * * *